(12) United States Patent
David et al.

(10) Patent No.: US 8,193,174 B2
(45) Date of Patent: Jun. 5, 2012

(54) RESPONSIVE LUMINESCENT LANTHANIDE COMPLEXES

(75) Inventors: Parker David, Durham (GB); Robert Pal, Durham (GB); Junhua Yu, Durham (GB)

(73) Assignee: University of Durham, Durham (GB)

( * ) Notice: Subject to any disclaimer, the term of this patent is extended or adjusted under 35 U.S.C. 154(b) by 927 days.

(21) Appl. No.: 11/913,991

(22) PCT Filed: May 11, 2006

(86) PCT No.: PCT/GB2006/001718
§ 371 (c)(1),
(2), (4) Date: Jun. 30, 2008

(87) PCT Pub. No.: WO2006/120444
PCT Pub. Date: Nov. 16, 2006

(65) Prior Publication Data
US 2008/0312431 A1    Dec. 18, 2008

(30) Foreign Application Priority Data

May 11, 2005  (GB) .................................. 0509604.5
May 19, 2005  (GB) .................................. 0526673.9
Jun. 29, 2005  (GB) .................................. 0513229.5

(51) Int. Cl.
*A61K 31/33* (2006.01)
*C07D 225/02* (2006.01)
*C07D 245/00* (2006.01)

(52) U.S. Cl. .......................... 514/183; 540/465; 540/470
(58) Field of Classification Search ........................ None
See application file for complete search history.

(56) References Cited

U.S. PATENT DOCUMENTS

| 5,622,821 | A | 4/1997 | Selvin et al. |
| 6,740,756 | B1 | 5/2004 | Chan et al. |
| 7,517,701 | B2 * | 4/2009 | Parker et al. .................. 436/546 |

FOREIGN PATENT DOCUMENTS

| WO | WO 0001663 A | 1/2000 |
| WO | WO 03035655 A | 5/2003 |
| WO | WO 2006/039505 A2 | 4/2006 |

OTHER PUBLICATIONS

Aime S; Batsanov A S; Botta M; Howard J A K' Lowe M P; Parker D: "Structure and relaxivity of macrocyclic gadolinium complexes incorporating pyridyl and 4-morpholinopyridyl substituents" New Journal of Chemistry, 1999, pp. 669-670, vol. 23.
Atkinson P; Findlay K S; Kielar F; Pal R; Parker D; Poole R A; Puschmann H; Richardson S L; Stenson P A; Thompson A L; Yu J: "Azaxanthones and azathioxanthones are effective sensitisers for europium and terbium luminescence" Organic & Biomolecular Chemistry, Mar. 23, 2006, pp. 1707-1722, vol. 4.
Bobba G; Cann M J; Frias J C; Parker D; Peacock R; Poole R A: "Synthesis and characterisation of highly emissive and kinetically stable lanthanide complexes suitable for usage 'in cellulo,'" Organic and Biomolecular Chemistry, Mar. 2, 2005, pp. 1013-1024, vol. 3.
Bretonniere Y; Cann M J; Parker D; Slater R: "Ratiometric probes for hydrogencarbonate analysis in intracellular or extracellular environments using europium luminescende" Chemical Communications, Jul. 30, 2002, pp. 1930-1931, vol. 2002.
Bruce J I; Dickins R S; Govenlock L J; Gunnlaugsson T; Lopinski S; Lowe M P; Paker D; Peacock R D; Perry J J B; Aime S; Botta M, The Selectivity of Reversible Oxy-Anion.
Binding in Aqueous Solution at a Chiral Europtium and Terbium Center: Signaling of Carbonate Chelation by changes in the Form and Circular Polarization of Luminescence Emission Journal of the American Chemical Society, Sep. 26, 2000, pp. 9674-9684, vol. 122.
Cann, M J; Pal, R; Parker, D; Poole, R A; Yu, J: "A Europium Complex that Selectively Stains Nucleoli of Cells," Journal of the American Chemical Society, Nov. 7, 2006 pp. 2294-2299, vol. 128.
Parker D; Yu J: "A pH-insensitive, ratiometric chemosensor for citrate using europium luminescence," Chemical Communications, May 20, 2005, pp. 3141-3143, vol. 2005.
Yu J; Parker D: "Synthesis of a Europium Complex for Anion-Sensing Involving Regioselective Substitution of Cyclen," European Joural of Organic Chemistry, Aug. 25, 2005 pp. 4249-4252, vol. 2005.

* cited by examiner

*Primary Examiner* — Noble Jarrell
(74) *Attorney, Agent, or Firm* — Berenato & White, LLC

(57) ABSTRACT

The invention provides a compound comprising a xanthone or thiaxanthone sensitizing moiety, capable of coordinating to a lanthanide ion by the nitrogen atom of an integral pyridyl group or a related group able to bind a lanthanide ion.

21 Claims, 5 Drawing Sheets

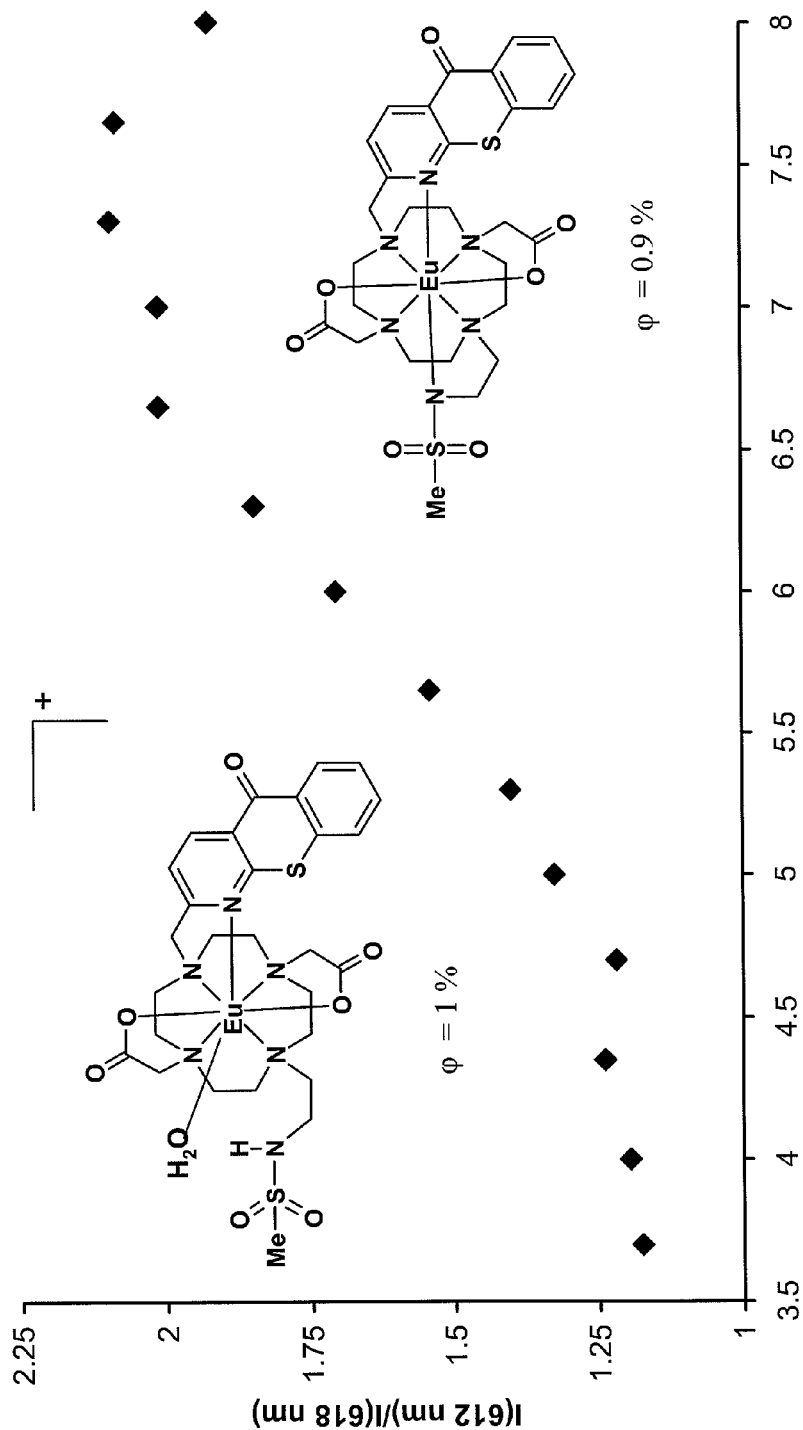

RESPONSIVE LUMINESCENT LANTHANIDE COMPLEXES

This application is a national stage application under 35 USC 371 of PCT/GB2006/001718, filed May 11, 2006.

This invention provides luminescent lanthanide complexes of europium and terbium, methods for their efficient sensitisation and their application in time-resolved assays of bioactive species.

INTRODUCTION

The unique magnetic and spectroscopic properties of the ground and excited states of the f block ions afford considerable scope for the development of new chemical entities that can be used as imaging probes, as components of optoelectronic devices, or as key sensor materials. Particular advantages of f-block ions are their intense, line-like and long-lived luminescence at a range of wavelengths spanning the visible and near infrared (NIR) regions, which permits time-gated rejection of unwanted signals arising from (short-lived) autofluorescence from biomolecules. Lanthanide chemistry accordingly plays a key role in such diverse areas as display technology and clinical diagnosis.

There is a need for simple modular synthetic routes that lead to stable emissive systems with tunable photophysical properties and high overall quantum yields (>10% for Eu/Tb in competitive media), that resist photo-fading and bleaching, and can be excited at longer wavelengths to minimise competitive absorption by endogenous molecules or tissue (at the very least, they should obviate the use of quartz optics). Moreover, they should, preferably, allow scope for conjugation to biomolecules, and should, preferably, be compatible with other probes to permit multiplexed imaging. Notwithstanding the burgeoning academic literature (e.g. Verhoeven, Bunzli, Raymond and Sammes (for example B H Bakker et al., *Coord. Chem. Rev.,* 2000, 208, 3; J C G Bunzli & C. Piguet, *Chem. Soc. Rev.,* 2005, 34, 1098; S. Petoud et al., *J. Am. Chem. Soc.,* 2003, 125, 13324; and A. Dadabhoy et al., *J. Chem. Soc. Perkin Trans* 2, 2000, 2359) reporting the chemistry of new emissive lanthanide(III) complexes or probes, no single molecule meets each of these criteria, and new approaches are required.

Moreover, organic chromophores have been widely used as sensitisers of lanthanide emission. However, very few of those possess a $S_1$-$T_1$ energy gap small enough to allow excitation at the longest possible wavelengths without detrimental back energy transfer from the excited state of the metal ion to the sensitiser $T_1$ state. This is a particularly demanding task for the visibly emitting lanthanides, since their high excited state energies restrict the range of possible sensitisers to those with relatively high triplet state energies. Acridones have been used for this purpose, but in polar media possess an inefficient inter-system crossing step, so that sensitiser fluorescence competes with triplet formation.

SUMMARY OF THE INVENTION

We have surprisingly found that the lanthanide complexes described herein (incorporating azaxanthone and azathioxanthone sensititsers) undergo efficient sensitized excitation and can be used in time-resolved assays of bioactive species, especially in signalling the variation in the local concentration of endogenous species such as pH or the citrate anion. In particular, the invention relates to luminescent lanthanide complexes incorporating a xanthone, thiaxanthone sensitising moiety, capable of coordinating to a lanthanide ion by an integral pyridyl group or a related group able to bind to a lanthanide ion. The resulting complex is able to emit light following excitation of the organic sensitising moiety and the emission characteristics are a function of the coordination environment.

Without wishing to be bound by theory, it is believed that whilst azaxanthone and thiaazaxanthone chromaphores have, like the acridones mentioned above, relatively high triplet state energies, they have the benefit of a faster rate of intersystem crossing in polar media, so that ligand fluorescence is much less prevalent. As a result of the small singlet-triplet energy gap, they allow sensitisation of a proximate lanthanide ion in the range 335-420 nm, away from co-absorption by many biomolecules. By engineering these chromophores into well-defined complexes, and using them as efficient sensitisers of lanthanide ions, in particular $Eu^{3+}$ and $Tb^{3+}$, we have developed highly emissive and stable systems.

Viewed from one aspect, therefore the invention provides a compound comprising a xanthone or thiaxanthone sensitising moiety, capable of coordinating to a lanthanide ion by the nitrogen atom of an integral pyridyl group or a related group able to bind a lanthanide ion.

Viewed from a further aspect, the invention provides a complex of a compound of this invention and a lanthanide ion, in particular a lanthanide (III) ion, still more particularly a europium (III) or terbium (III) ion.

In a further aspect of the present invention, the lanthanide complex is able to form a complex with another species, typically an anion. As a result, the emission spectral response of the lanthanide complex is modulated, allowing analysis of the signal by monitoring of two or more emission wavelengths, or by monitoring changes in emission lifetime or circular polarisation.

BRIEF DESCRIPTION OF THE DRAWINGS

The drawings illustrate selected characterisation data, and exemplify spectral response characteristics under the skilled conditions. In particular:

FIG. 5. shows the pH dependence of emission intensity (luminescence) ration of 613 to 617 nm of the Europium complex described in Example 4.

DETAILED DESCRIPTION OF THE INVENTION

Figure 1:
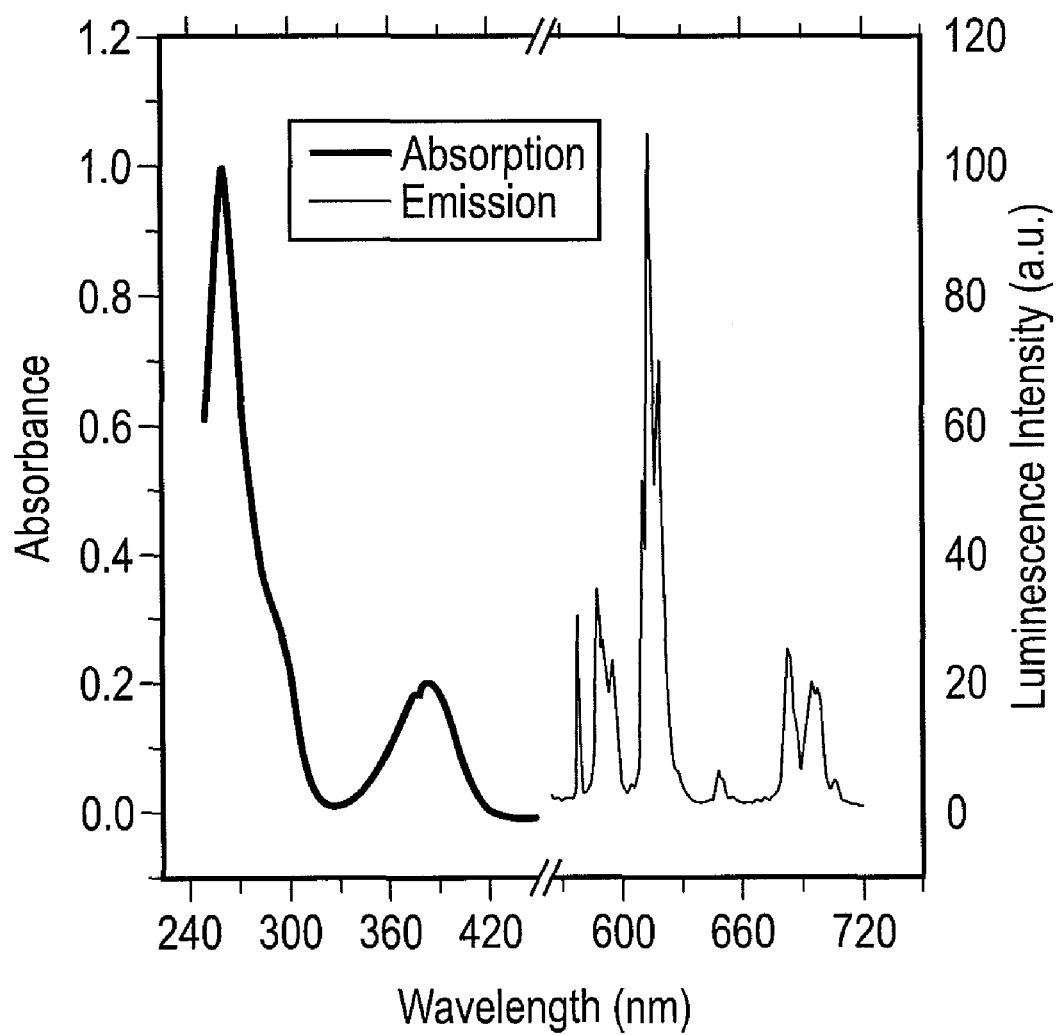
FIG. 1 shows the absorption and luminescence (emission) spectrum of $[EuL^1]^{3+}$ (see Example 1) in water.
Figure 2:
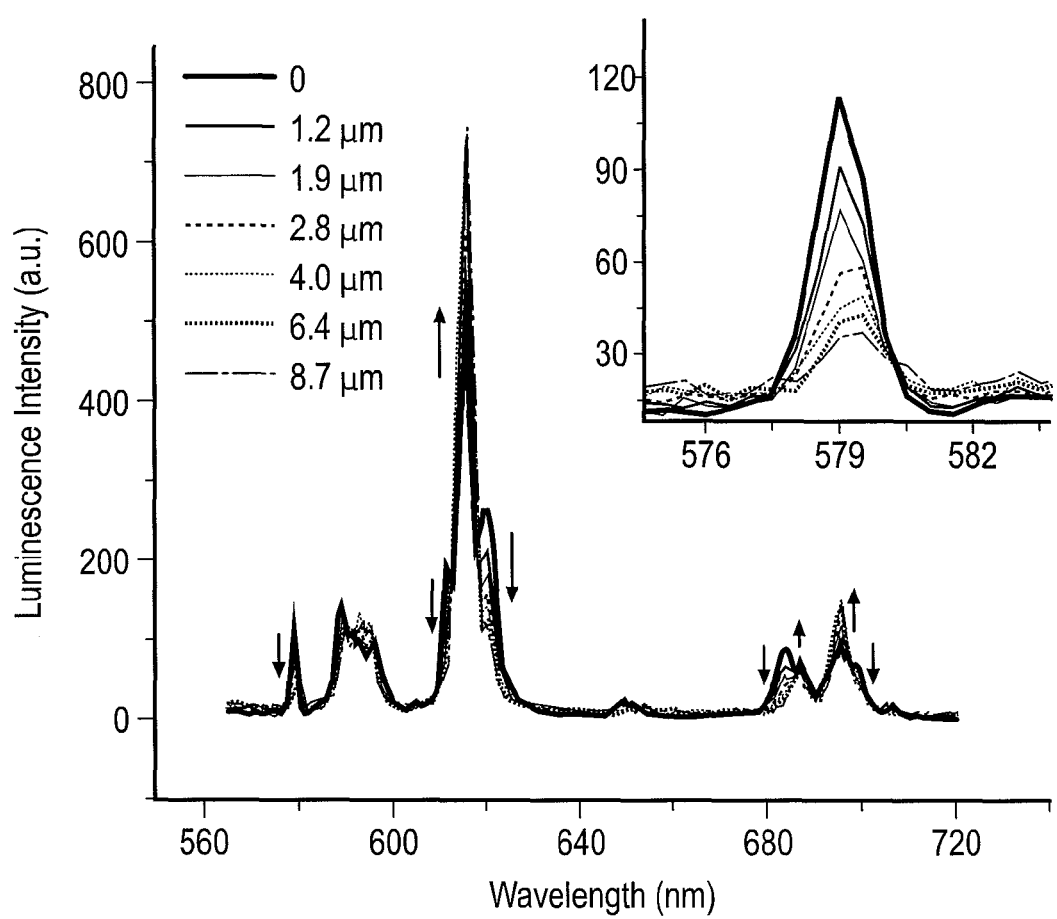
FIG. 2. shows the luminescence spectra and intensity ratio changes of an aqueous solution of $[EuL^1]^{3+}$ ($5\times10^6$ mol·$L^{-1}$) upon titration of sodium citrate; $\lambda_{exc}$=384 nm.
Figure 3:
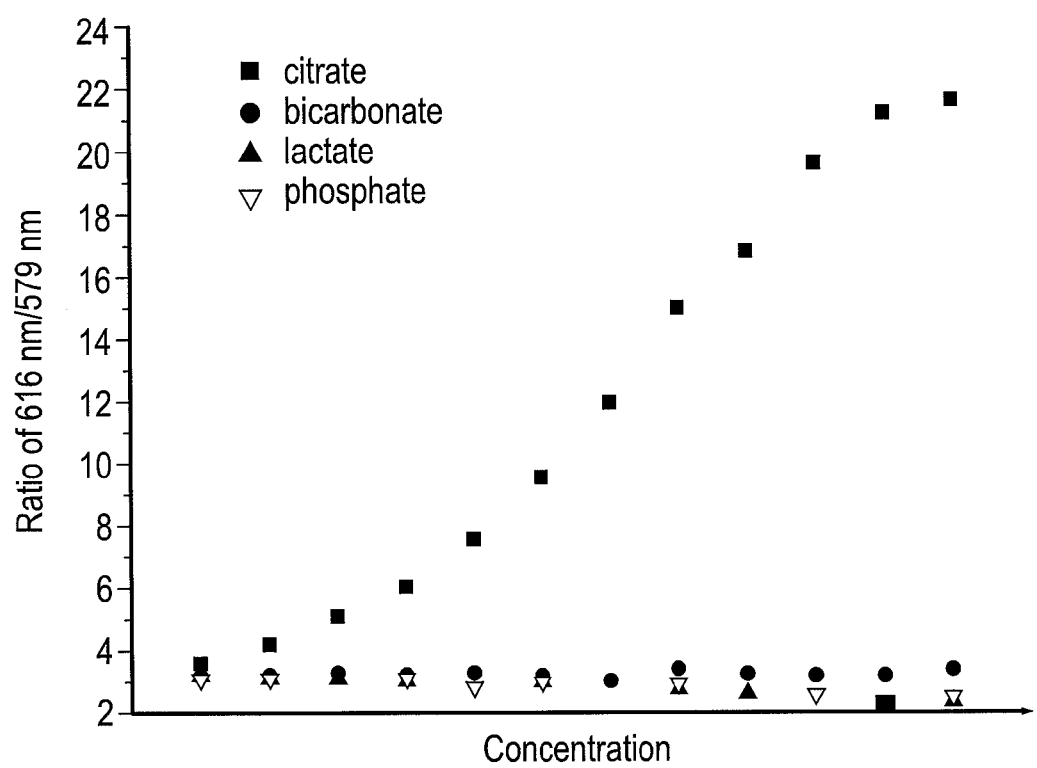
FIG. 3. shows the luminescence intensity ratio of 616 nm to 579 nm of an aqueous solution of $[EuL^1]^{3+}$ ($5\times10^{-6}$ mol·$L^{-1}$) upon the titration of citrate, phosphate, bicarbonate, lactate, respectively; excited at 384 nm. Here it shows clearly that, among these anions, only citrate exhibits good affinity to the complex.
Figure 4:
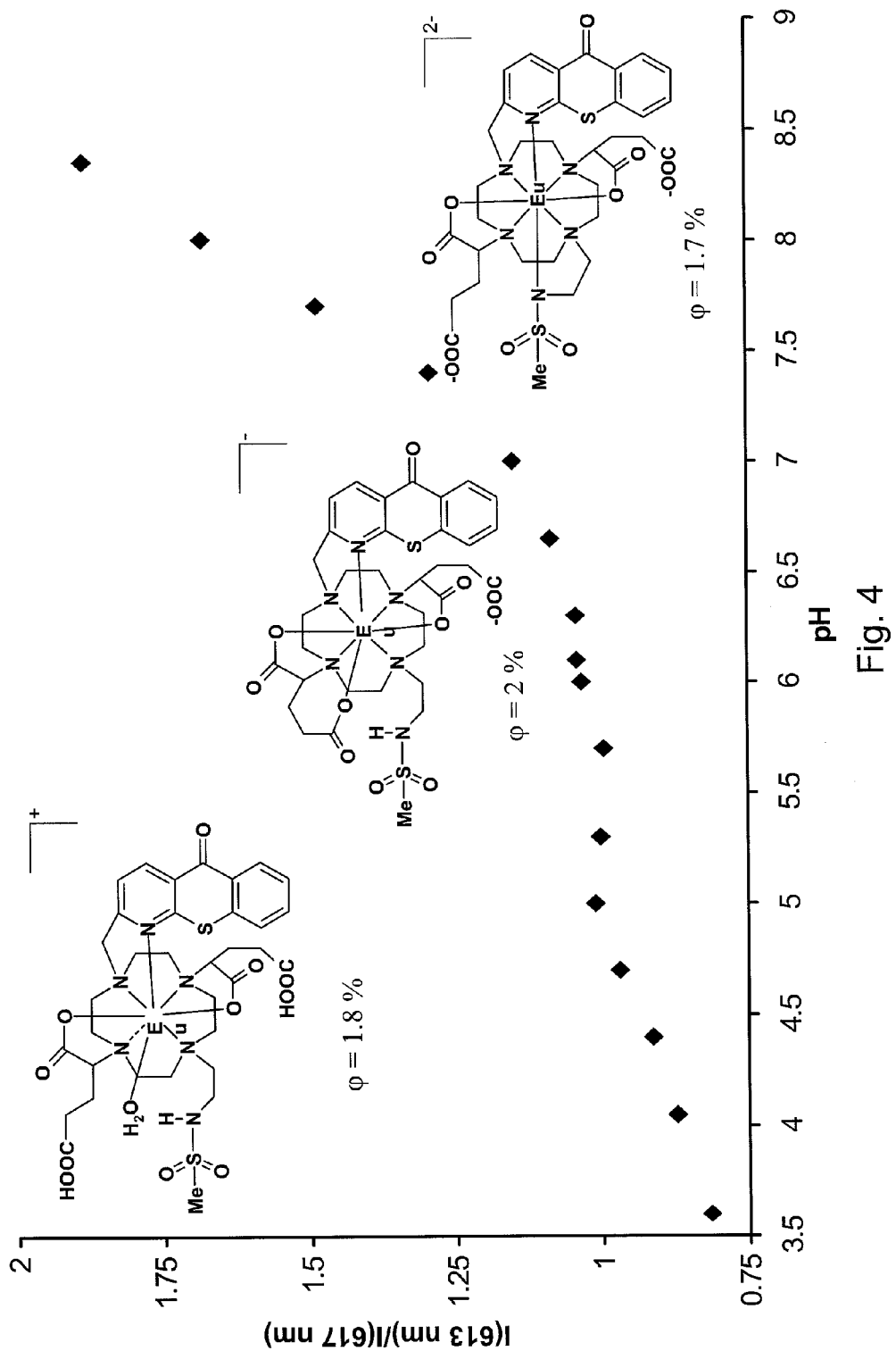
FIG. 4. shows the pH dependence of emission intensity (luminescence) ratio of 612 to 618 nm of the Europium complex described in Example 3.

The compounds of the invention each comprise xanthone or thiaxanthone sensitising moiety, capable of coordinating to a lanthanide ion by the nitrogen atom of an integral pyridyl group or a related group able to bind a lanthanide ion. Preferably the compounds are of the general structures 1, 2 or 3 shown below:

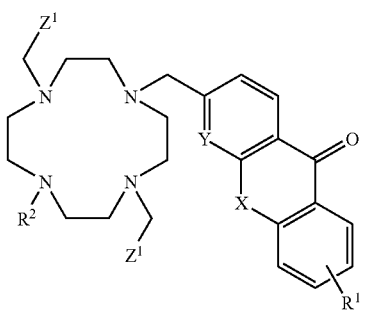

1

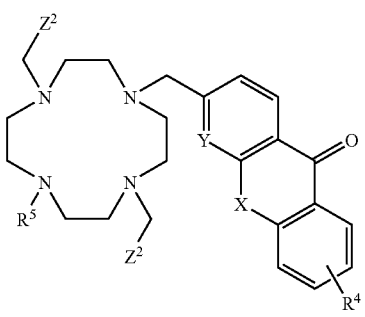

2

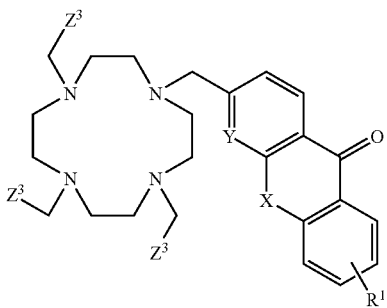

3

(wherein:
R¹ is H, alkyl, aralkyl, $CO_2R^3$, $CONHR^3$;
R² is H, alkyl or aralkyl;
R³ is alkyl, aralkyl or aryl, optionally substituted;
R⁴ is H, alkyl, aralkyl, $CO_2R^6$;
R⁵ is $CH_2CH_2NHSO_2R^6$;
R⁶ is alkyl, p-R⁴-Ph, p-OMe-Ph, p-$CF_3$-Ph;
X is O or S;
Y is N, N-oxide or C—OH
$Z^1$ is $CO_2^-$, $PR^1O_2^-$, $PO_3^{2-}$, $CONHR^3$;
$Z^2$ is $CO_2^-$, $PR^4O_2^-$, $PO_3^{2-}$, $CONHR^4$; and
$Z^3$ is $CO_2^-$, $PR^1O_2^-$, $PO_3^{2-}$, $CONHR^1$).

In 1, X may be S or O (preferably S), Y is preferably N, but may also be an N-oxide group or a hydroxy group attached to C, and Z is a carboxylate, phosphinate, phosphonate or carboxamide. The complex is coordinatively unsaturated and is therefore able to bind to an added anion or other electron-rich species, as exemplified in the details given below for [EuL¹] (see Example 1), where Y=N, X=S, R²=H, $Z^1$=(S)—CONHCH($CH_2$Ph)$CO_2$Et and R¹=H.

In 2, (wherein X and Y are as defined for 1) a substituent on the 12-ring macrocycle, is able to bind reversibly to the lanthanide ion. This coordination is modulated by variations in pH. The alkylsulfonamide substituent R⁶ may be any alkyl or aralkyl group, particularly R=Me, p-tolyl, p-methoxyphenyl or p-trifluoromethylphenyl.

In 3, X may be S or O (preferably S), Y is preferably N, but may also be an N-oxide group or a hydroxy group attached to C, and Z is a carboxylate, phosphinate, phosphonate or carboxamide. The complex is coordinatively unsaturated and is therefore able to bind to an added anion or other electron-rich species.

In each of the compounds of the invention, Y is preferably nitrogen and, independently, X is preferably sulfur.

Examples of compounds of the invention, which are described in the Examples which follow below, are 1-(2'-[1-azathioxanthone]methyl)-4,10-bis[(S,S)-ethyl-2"-carbamoylmethyl-3-phenylpropanoate]-1,4,7,10-tetra-azacyclododecane, 4-[(1-azathioxanthone)-2-methyl]-1,7-bis(carboxymethyl)-1,4,7,10-tetra azacyclododecane, 4-[(1-azathioxanthone)-2-methyl]-10-[methylsulfonylamino)ethyl]-1,7-bis(carboxymethyl)-1,4,7,10-tetraazacyclododecane and 4-[(1-azathioxanthone)-2-methyl]-10-[methylsulfonylamino)ethyl]-1,7-bis(α-glutarate)-1,4,7,10-tetraazacyclododecane.

The compounds of the invention may be used to provide luminescent lanthanide complexes by binding to a lanthanide ion. Exemplary of such complexes are those shown below in structures 4, 5 and 6 in which the substituents have the same meanings as set forth in relation to formulae 1 to 3:

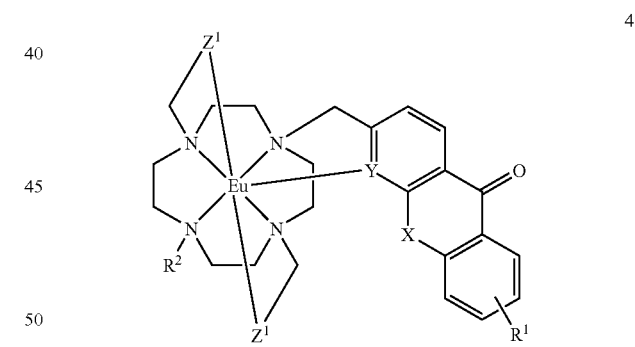

4

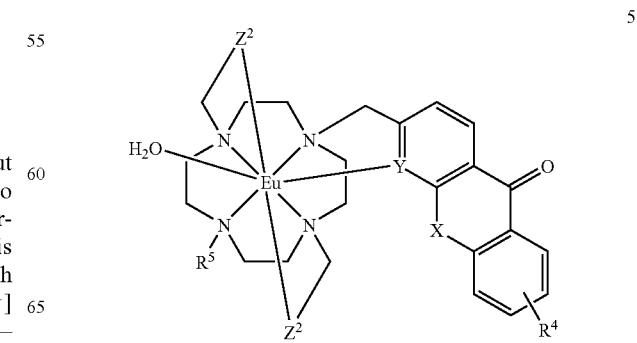

5

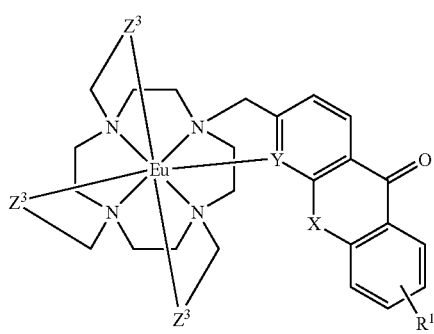

In the structure of the examples shown, the direct coordination of the chromophore to the lanthanide ion minimises the separation between sensitiser and the acceptor lanthanide ion ensuring efficient energy transfer.

The range of anions which may bind includes phosphono-anions, e.g. phospho tyrosine (serine or threonine) sites in peptides or proteins, citrate, lactate, hydrogencarbonate or related species capable of chelating to a lanthanide (III) centre. Selective binding to citrate is preferred. The formulation of further complexes by complexation with other species forms a further aspect of this invention. Viewed from this aspect the invention provides a method of modulating a complex as defined herein comprising reacting the complex with a ligand, typically an anion as defined herein.

In a related aspect, the complex contains a sub-structure that is able to bind reversibly to the lanthanide ion as a function of pH. This intramolecular ligation is signalled by a change in the emission spectral profile of the lanthanide ion, e.g. by changes in two or more emission wavelength intensities or in the lifetime or circular polarisation of emission. In a preferred aspect, an alkylsulfonamide group, linked to the core ligand structure by a carbon-nitrogen bond, is incorporated in the complex structure and reversibly binds to the lanthanide ion over the pH range 3 to 9, especially the range 4.5 to 8. Such behaviour allows the monitoring of local pH using the lanthanide complex as a probe, as required for monitoring local pH changes in real time using ratiometric methods of analysis in analytes ranging from typical in vitro situations to in cellulo or in vivo assays or applications, as required in time resolved luminescence imaging using microscopy or spectroscopy.

The invention is now illustrated by the following examples, which are not to be considered as limiting of the invention. These describe the synthesis and characterization of representative Eu complexes; the synthetic schemes employed will be evident to those skilled in the art. The figures illustrate the spectral response of certain complexes in the presence of selected anions.

EXAMPLE 1

Preparation of 1-(2'-[1-azathioxanthone]methyl)-4,10-bis[(S,S) ethyl-2"-carbamoylmethyl-3-phenylpropanoate]-1,4,7,10-tetra-azacyclododecane ($L^1$) and europium (III) complex thereof (i) Synthesis of 3-Chloromethylpyridothioxanthone

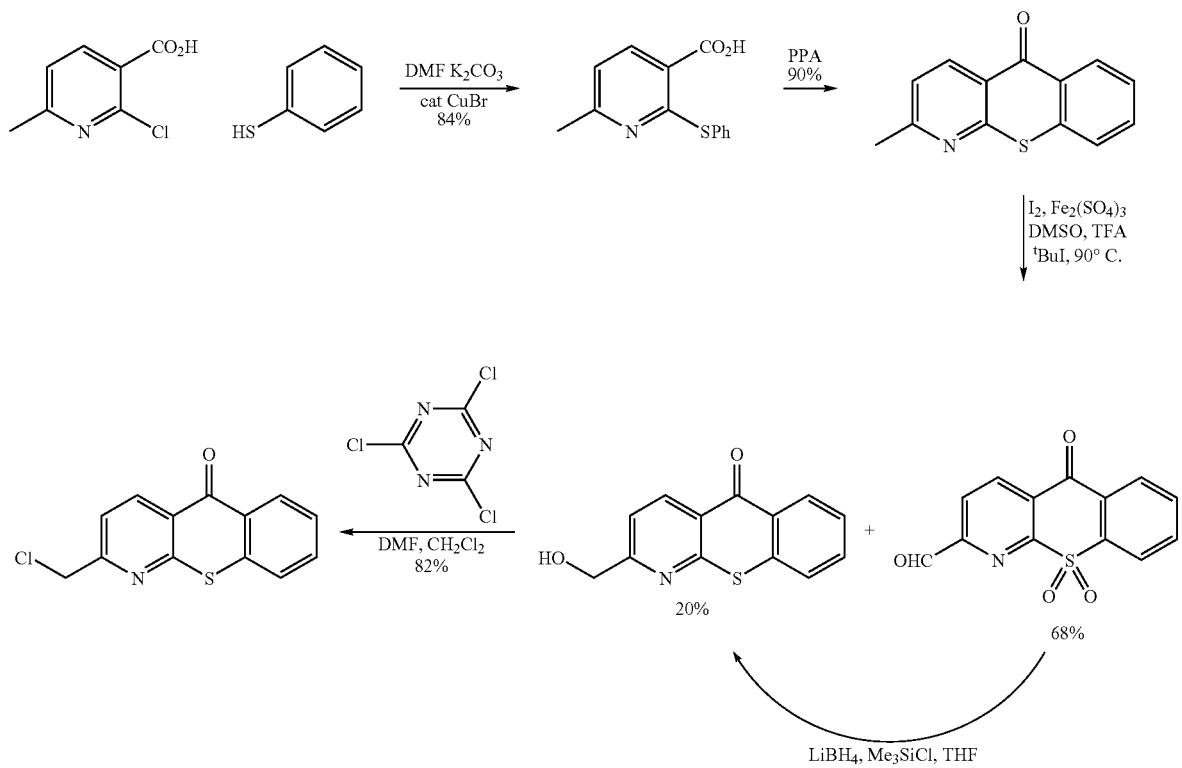

Synthesis of 6-methyl-2-phenylthionicotinic acid, 1

To 3-chloro-6-methylnicotinic acid (5 g, 29 mmol), thiophenol (3.8 g, 34 mmol, 1.2 eq.) and copper (I) bromide (0.25 g), in DMF (30 mL) was added potassium carbonate (6 g), and the stirred mixture was heated at 130° C. for 15 min. After being heated at 150° C. overnight and cooled down, the mixture (light yellow) was diluted with water (170 mL) and washed with ethyl ether (80 mL×3). The aqueous solution was acidified with acetic acid to pH 4.5, resulting in a pale yellow precipitate. The solid was filtered, washed with water and dried under reduced pressure to give a yellow solid (5.9 g, 83%). $^1$H-NMR (DMSO-$d_6$): 13.40 (1H, s, —COOH), 8.13 (1H, d, J 7.2, $H_1$), 7.42-7.52 (5H, m, $H_2$,–$H_6$), 7.09 (1H, d, J 7.2, $H_2$), 2.23 (3H, s, $CH_3$). m/z ($ES^+$): 246 $[M+H]^+$, 268 $[M+Na]^+$.

Synthesis of 3-methylpyridothioxanthone, 2

The acid 1 (5.5 g, 22 mmol) and polyphosphoric acid (60 mL) were heated at 120° C. for 4 hrs. The solid dissolved and the solution became brown. The mixture was added to a concentrated aqueous sodium hydroxide solution (300 mL) slowly with vigorous stirring. A precipitate formed. Further sodium hydroxide pellets were added to yield a pH 8 solution. The solution was filtered and the precipitate was washed with water and dried under reduced pressure to give a yellow solid (4.6 g, 90%); m.p. 145-146° C. $^1$H-NMR (DMSO-$d_6$): 8.73 (1H, d, J 8.2, $H_1$), 8.60 (1H, d, J 8.4, $H_8$), 7.65-7.67 (2H, m, $H_5$+$H_6$), 7.48-7.56 (1H, m, $H_7$), 7.31 (1H, d, J 8.2, $H_2$), 2.70 (3H, s, $CH_3$). m/z ($ES^+$): 228 $[M+H]^+$, 250 $[M+Na]^+$, 477 $[2M+Na]^+$.

3-Hydroxymethyl-4-pyridothioxanthone, 3, and pyridothioxanthen-9-one-10,10-dioxide-3-carboxaldehyde, 4

A solution of 3-methylpyridothioxanthone (3.2 g, 14 mmol), iodine (4.3 g, 17 mmol), iron(III) sulfate pentahydrate (1.2 g, 2.9 mmol), and DMSO (50 mL) was stirred for 5 min, and then tert-butyl iodide (1 mL, 8.7 mmol) and trifluoroacetic acid (3 mL) were added. The mixture was heated at 90° C. for 6 hrs, then cooled to room temperature, following the addition of aqueous sodium thiosulfate solution (15 mL). The mixture was stirred at r.t. for 1 hr, and then diluted with DCM (400 mL). The solution was washed with water (100 mL×5), and dried over sodium sulfate anhydrous. The mixture was purified by column chromatography on silica gel, with DCM as the eluant to yield first pyridothioxanthen-9-one-10,10-dioxide-3-carboxaldehyde, then with DCM/methanol (125:4) 3-hydroxymethyl-4-pyridothioxanthone, yielding 2.1 g (68%) and 0.7 g (20%), respectively.

A mixture of lithium borohydride (0.24 g, 12 mmol) and trimethylsilylchloride (1.4 mL, 12 mmol) in 20 mL of THF was added dropwise into a solution of pyridothioxanthen-9-one-10,10-dioxide-3-carboxaldehyde (1.6 g, 5.9 mmol) in THF in 0° C. The solution was stirred for a further 2 hrs before adding water (8 mL). The solvents were removed under reduced pressure, giving a yellow solid which was sonicated in a mixture of DCM (300 mL) and 0.5 M hydrochloric acid (100 mL). The organic phase was washed with water, and dried over sodium sulfate. The mixture was purified by column chromatography on silica gel, eluting with DCM/methanol (125:4) to yield 3-hydroxymethyl-4-pyridothioxanthone, (0.5 g, 35%).

pyridothioxanthen-9-one-10,10-dioxide-3-carboxaldehyde: $^1$H-NMR (CDCl$_3$): 10.16 (1H, d, J 1, CHO), 9.00 (1H, dd, J 1.0, 8.0, $H_2$), 8.62 (1H, d, J 8.0, $H_8$), 8.02 (1H, d, J 8.0, $H_1$), 7.74-7.70 (2H, m, $H_5$+$H_6$), 7.61-7.53 (1H, m, $H_7$)). m/z ($ES^+$): 296 $[M+Na]^+$.

3-hydroxymethyl-4-pyridothioxanthone: $^1$H-NMR (CDCl$_3$): 8.85 (1H, d, J 8.2, $H_1$), 8.62 (1H, d, J 10.0, $H_8$), 7.73-7.66 (2H, m, $H_5$+$H_6$), 7.57-7.53 (1H, m, $H_7$), 7.41 (1H, d, J 10.0, $H_2$), 4.92 (2H, s). m/z ($ES^+$): 244 $[M+H]^+$, 266 $[M+Na]^+$, 509 $[2M+Na]^+$.

3-Chloromethylpyridothioxanthone, 5

A solution of cyanuric chloride (0.29 g, 0.16 mmol) in DMF (1 mL) was stirred for 0.5 hrs, resulting in a white precipitate. Dichloromethane (30 mL) was added, followed by a solution of 3-hydroxymethylpyridothioxanthone (0.25 g, 1.0 mmol) in DCM (20 mL). The solution was stirred at r.t. overnight, then washed with hydrochloric acid (0.5 M, 30 mL) and water, and then dried over sodium sulfate. The mixture was purified by column chromatography on silica gel with DCM/hexane (2:3) as the eluant, yielding 3-chloromethylpyridothioxanthone (0.22 g, 82%). $^1$H-NMR (CDCl$_3$): 8.88 (1H, d, J 8.4, $H_1$), 8.61 (1H, d, J 8.1, $H_8$), 7.73-7.64 (3H, m, $H_2$+$H_5$+$H_6$), 7.57-7.52 (1H, m, $H_7$), 4.76 (2H, s)). m/z ($ES^+$): 262 $[M+H]^+$, 284 $[M+Na]^+$, 545 $[2M+Na]^+$.

(ii) Synthesis of bromoacetylphenylalanine ethyl ester, 6

Under argon, bromoacetyl bromide (0.89 g, 10.2 mmol) in chloroform (10 mL) was added dropwise to a mixture of chloroform (40 mL), L-phenylalanine ethyl ester (2.3 g, 10 mmol), and triethylamine (3 mL), which was pre-cooled to −30° C. The mixture was stirred at r.t. for a further 2 hrs, and then washed with aqueous saturated potassium carbonate solution and water, then dried over sodium sulfate. The solvents were removed under reduced pressure, giving a dark oil, which was dissolved in a mixture of DCM (100 mL) and hexane (300 mL), form which a crystalline solid deposited. The crystals were dried in air, giving colourless needles (2.7 g, 79%). $^1$H-NMR (CDCl$_3$): 7.29-7.31 (3H, m, Ar), 7.11-7.16 (2H, m, Ar), 4.79-4.89 (1H, m, α-H), 4.20 (2H, q, J 7.2, OCH$_2$CH$_3$), 3.86 (2H, s, BrCH$_2$), 3.16 (2H, d, J 5.8, ArCH$_2$), 1.26 (3H, t, J 7.2, OCH$_2$CH$_3$). m/z ($ES^+$): 336 $[M+Na]^+$.

Synthesis of Cbz-protected cyclen, 7

To a suspension of 1,4,7,10-tetraazacyclododeane (5 g, 29 mmol) and Na$_2$HPO$_4$ (14 g) in a mixture of water (50 mL) and dioxane (20 mL), concentrated hydrochloric acid was added to adjust the pH value of the solution to 2.5-3.0, and the solid in the solution dissolved. Benzyl chloroformate (12 g, 70 mmol) in dioxane (20 mL) was then added to the above mixture dropwise. The solution was stirred at r.t. for 18 hrs, giving a white precipitate in the mixture. The solvents were removed to yield a white mush which was then washed with 50 mL ethyl ether. Water (100 mL) was added to the mush and the pH was tuned back to neutral with concentrated aqueous sodium hydroxide solution. The above aqueous solution was extracted with ethyl ether (150 mL×3). The ether was collected, dried over anhydrous sodium sulfate, and evaporated to yield a viscous oil (10 g, 78%). $^1$H-NMR (CDCl$_3$): 7.26-7.21 (10H, m, ArH); 5.05 (4H, s, ArCH$_2$O); 3.33 (8H, br s, cyclen); 2.74 (8H, m, cyclen). m/z ($ES^+$): 441 $[M+H]^+$, 463 $[M+Na]^+$, 903 $[2M+Na]^+$.

Cbz-protected Phe ester cyclen, 8

Under argon, 7 (2.4 g, 4.5 mmol), N-(2-bromoacetyl)phenylalanine ethyl ester (3.2 g, 10.0 mmol), potassium carbonate (8.5 g), in DMF (50 mL) were stirred at r.t. overnight. Then DCM (200 mL) was added, and the solution was washed with water (100 mL×10); dried over anhydrous potassium carbonate. The solvents were removed under reduced pressure, resulting in an oily product (4.3 g, 98%). $^1$H-NMR (CDCl$_3$): 7.19-7.34 (20H, m, ArH); 5.08 (4H, s, ArCH$_2$O); 4.81 (2H, m, α-H (Phe)); 4.18 (4H, t, J 7.2, OCH$_2$CH$_3$); 3.32 (8H, br s, cyclen); 3.11 (8H, br s, NCH$_2$ and ArCH$_2$C); 2.76 (8H, br s, cyclen); 1.19 (6H, t, J 7.2, OCH$_2$CH$_3$). m/z (ES$^+$): 908 [M+H]$^+$.

Phe ester cyclen, 9

The ester 8 (4.1 g, 4.5 mmol) was dissolved in ethanol (50 mL) and hydrogenated over 0.1 g of Pd/C (20%, w/w) and 40 psi of hydrogen at room temperature for 4 days. The solvents were removed under reduced pressure, giving a colourless oil. The product was re-crystallised from ethyl ether and DCM, yielding 0.7 g light yellow solid product, and 2.0 g of an oily product; the latter slowly solidified, (total 93%). $^1$H-NMR (CDCl$_3$): 7.30-7.15 (10H, m, ArH); 4.89 (2H, m, α-H (Phe)); 4.20 (4H, q, J 7.2, OCH$_2$CH$_3$); 3.25 (8H, br s, NCH$_2$ CO and ArCH$_2$C); 2.75 (16H, br s, cyclen); 1.30 (6H, t, J 7.2, OCH$_2$CH$_3$). m/z (ES$^+$): 640 [M+H]$^+$.

Phe ester cyclen pyridothioxanthone: 1-(2'-[1-azathioxanthone]methyl)-4,10-bis[(S,S)-ethyl-2''-carbamoylmethyl-3-phenylpropanoate]-1,4,7,10-tetra-azacyclododecane (L$^1$)

Under argon, 9 (1.5 g, 2.2 mmol), 3-chloromethylpyridoxanthone (0.3 g, 1.1 mmol), and 5 g of potassium carbonate were stirred in acetonitrile (40 mL) at r.t. for 48 hrs. Then DCM (200 mL) was added and the solution was washed with water (80 mL×3), and dried over sodium sulfate. The product was purified by column chromatography on alumina with DCM/EtOAc/CH$_3$OH (250:15:4) as eluant, yielding a light yellow solid product (0.32 g, 34%). $^1$H-NMR (CDCl$_3$): 8.77 (1H, d, J 8.0, H$_1$), 8.60 (1H, d, J 8.0, H$_8$), 7.71-7.65 (2H, m, H$_5$+H$_7$), 7.59-7.51 (2H, m, H$_2$+H$_6$), 7.31-7.12 (10H, m, ArH); 4.81 (2H, m, α-H (Phe)); 4.15 (4H, q, J 7.2, OCH$_2$CH$_3$); 3.82 (2H, s, ArCH$_2$N); 3.26-3.16 (8H, m, cyclen); 3.04 (4H, s, NCH$_2$CO); 2.82 (4H, br s, cyclen); 2.77 (4H, br s, cyclen); 2.05 (4H, s, ArCH$_2$C); 1.23 (6H, t, J 7.2, OCH$_2$CH$_3$). m/z (ES$^+$): 865 [M+H]$^+$;
HRMS (ES$^+$), found: 864.4191; C$_{47}$H$_{58}$O$_7$N$_7$S requires: 864.4197.

[EuL$^1$]$^{3+}$

Under argon, ligand 10 (80 mg, 0.09 mmol) and Eu(CF$_3$SO$_3$)$_3$ (134 mg, 0.26 mmol) were boiled under reflux in acetonitrile (3 mL) for 48 hrs. The solution was added slowly to diethyl ether (500 mL). The mixture was filtered. The crude product was dissolved in a mixture of DCM (20 mL) and toluene (6 mL). The solution was slowly evaporated at ambient pressure; when most of the DCM had evaporated a precipitate was collected, yielding a grey solid (60 mg, 44%). HRMS (ES$^+$), found: 1314.2311; C$_{49}$H$_{57}$O$_{13}$N$_7$EuF$_6$S$_3$ requires: 1314.23

EXAMPLE 2

Preparation of 4-[(1-azathioxanthone)-2-methyl]-1,7-bis(carboxymethyl)-1,4,7,10-tetra-azacyclododecane

(i) Preparation of 4-[(1-Azathioxanthone)-2-methyl]-1,7-bis(tert-butoxycarbonylmethyl)-1,4,7,10-tetraazacyclododecane

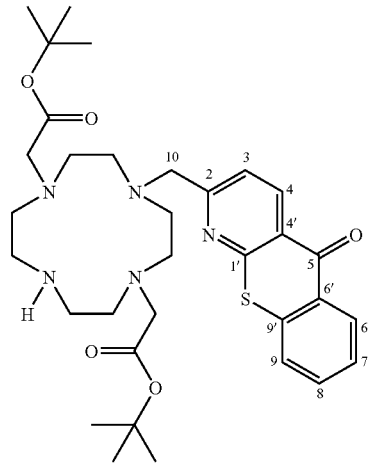

1,7-Bis(tert-butoxycarbonylmethyl)-1,4,7,10-tetraazacyclododecane (250 mg, 0.62 mmol) was combined with 2-bromomethyl-1-azathiaxanthone (1.1 eq., 190 mg) and K$_2$CO$_3$ (1 eq., 86 mg) and the mixture stirred in dry MeCN (12 mL) at reflux under argon for 18 h. The reaction was monitored by TLC (DCM:MeOH, 97:3) and ESMS$^+$ to confirm that the brominated starting material had been consumed. The solvent was removed under reduced pressure. The resulting solid was dissolved in a small volume of DCM (5 mL) and the KBr/K$_2$CO$_3$ was filtered out. The crude mixture was purified by column chromatography (DCM-2% MeOH) to yield the title compound as a yellow oil (161 mg, 0.258 mmol, 42%) $\delta_H$ (CDCl$_3$) 8.71 (1H, H$^4$, d, J 8.1 Hz), 8.60 (1H, H$^6$, d, J 8.0 Hz), 7.68 (2H, H$^{8,9}$, m), 7.49 (1H, H$^7$, m), 7.30 (1H, H$^3$, d, J 8.1 Hz), 3.87 (2H, H$^{10}$, s), 3.13-2.78 (4H, CH$_2$CO$_2$+16H, NCH$_2$CH$_2$N, m), 1.42 (18H, $^t$Bu, s) $\delta_c$ (CDCl$_3$) 180.7 (C$^5$), 170.2 (CO$_2$tBu), 161.3 (C$^2$), 158.6 (C$^{1'}$), 139.2 (C$^4$), 137.5 (C$^6$), 133.3 (C$^8$), 130.2 (C$^6$), 129.3 (C$^{9'}$), 127.5 (C$^7$), 127.1 (C$^9$), 124.8 (C$^{4'}$), 122.2 (C$^3$), 80.9 (CMe$_3$), 52.4 (C$^{10}$), 57.9 (CH$_2$CO$_2$), 50.1, 47.8 (NCH$_2$ CH$_2$N), 27.8 (CH$_3$), m/z (ESMS$^+$) 626 (M+1); R$_f$ 0.18 (DCM-3% MeOH, alumina plate)

(ii) Preparation of 4-[(1-azathioxanthone)-2-methyl]-1,7-bis(carboxymethyl)-1,4,7,10-tetra-azacyclododecane

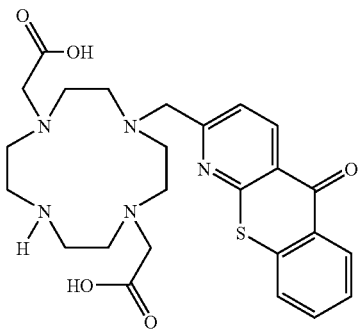

A mixture of trifluoroacetic acid (0.7 mL) and dichloromethane (0.3 mL) was added to 4-[(1-azathioxanthone)-2-methyl]-1,7-bis(tert-butoxycarbonylmethyl)-1,4,7,10-tetra-azacyclododecane (20 mg, 32 µmol) and the mixture stirred under argon at room temperature for 36 h. The solvents were removed under reduced pressure and a small volume of DCM (3×3 mL) was added and removed again under reduced pressure. The crude mixture was dissolved in water (3 mL) and extracted with DCM (3 mL) thrice, and lyophilised to yield the title compound as a pale-orange oil as the trifluoroacetate salt (14 mg, 27 µmol, 86%) which was used in a complexation reaction immediately. m/z (ESMS$^+$) 672 (M+2Na (CF$_3$COO))

(iii) Preparation of Eu-Complex

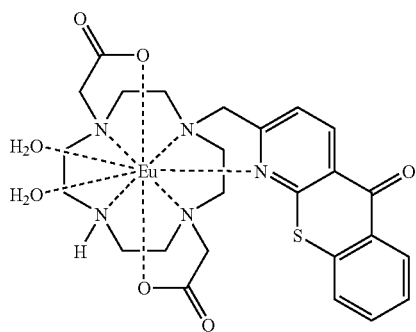

4-[(1-Azathioxanthone)-2-methyl]-1,7-bis(carboxymethyl)-1,4,7,10-tetraazacyclododecane (14 mg, 27 µmol) along with Eu(CF$_3$SO$_3$)$_3$ (1.1 eq., 18 mg) was dissolved in MeCN (1 mL) and the reaction left stirred at reflux temperature for 18 hrs. After the reaction was cooled to room temperature the solvents were removed under reduced pressure, the remaining residue was dissolved in 5 mL H$_2$O: MeOH (51). The pH was then adjusted carefully to 10 by addition of conc. NaOH solution (in order to get rid of the Eu-excess as Eu(OH)$_3$) resulting in a white precipitates removed via a fine syringe filter. The pH was adjusted back to neutral and lyophilised to give the desired complex as a pale yellow solid.

EXAMPLE 3

Preparation of 4-[(1-Azathioxanthone)-2-methyl]-10-[methyl-sulfonylamino)ethyl]-1,7-bis(carboxymethyl)-1,4,7,10-tetraazacyclododecane (i) Preparation of 4-[(1-Azathioxanthone)-2-methyl]-10-[methylsulfonylamino)ethyl]-1,7-bis(tert-butoxycarbonylmethyl)-1,4,7,10-tetraazacyclododecane

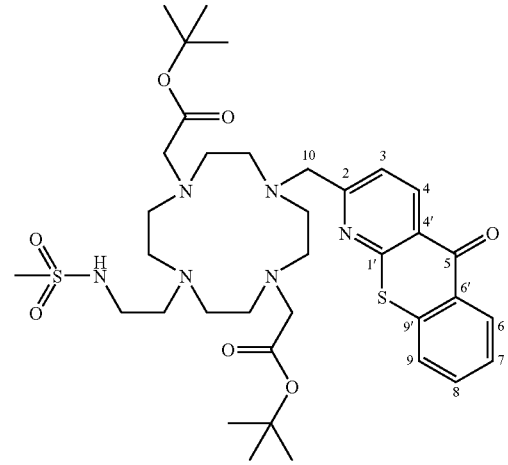

4-[(1-Azathioxanthone)-2-methyl]-1,7-bis(tert-butoxycarbonylmethyl)-1,4,7,10-tetra-azacyclododecane (87 mg, 0.14 mmol) was combined with N-methanesulfonyl-aziridine (1.1 eq., 17.3 mg) and K$_2$CO$_3$ (1 eq., 19 mg) stirred in dry MeCN (8 mL) at reflux under argon for 24 h. The reaction was monitored by TLC (DCM:MeOH, 97:3) and ESMS$^+$ to confirm that the starting secondary amine had been consumed. The solvent was removed under reduced pressure. The resulting solid was dissolved in a small volume of DCM (3 mL) and the K$_2$CO$_3$ was filtered out. The crude mixture was purified by column chromatography (DCM→2% MeOH) to yield the title compound as a light brown oil (72 mg, 97 µmol, 69%). $\delta_H$ (CDCl$_3$) 8.71 (1H, H$^4$, d, J 8.0 Hz), 8.60 (1H, H$^6$, d, J 8.0 Hz), 7.68 (2H, H$^{8,9}$, m), 7.49 (1H, H$^7$, m), 7.31 (1H, H$^3$, d, J 8.0 Hz), 3.90 (2H, H$^{10}$, s), 3.13-2.78 (4H, CH$_2$CO$_2$+16H, NCH$_2$CH$_2$N+4H, SO$_2$NHCH$_2$CH$_2$N m),), 2.01 (3H, SO$_2$CH$_3$), 1.41 (18H, $^t$Bu, s) $\delta_C$ (CDCl$_3$) 180.7 (C$^5$), 170.2 (CO$_2$tBu), 161.3 (C$^2$), 158.6 (C$^{1'}$), 139.2 (C$^{4'}$), 137.5 (C$^6$), 133.3 (C$^8$), 130.2 (C$^6$), 129.3 (C$^{9'}$), 127.5 (C$^7$), 127.1 (C$^9$), 124.8 (C$^4$), 122.2 (C$^3$), 81.1 (CMe$_3$), 67.0, 67.8 (SO$_2$NHCH$_2$CH$_2$N), 52.4 (C$^{10}$), 57.9 (CH$_2$CO$_2$), 50.1, 47.8 (NCH$_2$ CH$_2$N), 38.5 (SO$_2$CH$_3$), 27.8 (C(CH$_3$)$_3$), m/z (ESMS$^+$) 746 (M+1), 747 (M+2), 768 (M+Na); R$_f$ 0.44 (DCM:MeOH, 97:3, alumina plate)

(ii) Preparation of 4-[(1-Azathioxanthone)-2-methyl]-10-[methylsulfonylamino)ethyl]-1,7-bis (carboxymethyl)-1,4,7,10-tetraazacyclododecane

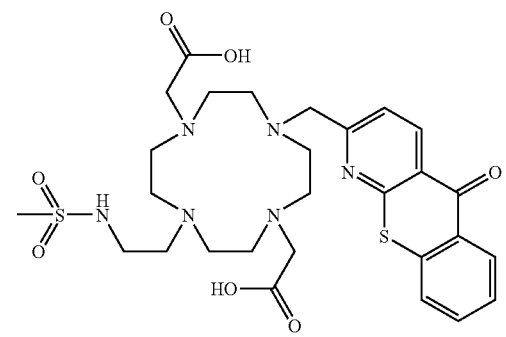

A mixture of trifluoroacetic acid (1.5 mL) and DCM (0.5 mL) was added to 4-[(1-azathioxanthone)-2-methyl]-10-[methylsulfonylamino)ethyl]-1,7-bis(tertbutoxy-carbonylmethyl)-1,4,7,10-tetraazacyclododecane (72 mg (97 μmol) and the reaction stirred under argon at room temperature for 28 h. The solvents were removed under reduced pressure and a small volume of DCM (3×3 mL) was added and removed again under reduced pressure. The crude mixture then had been dissolved in water (5 mL) and extracted with DCM (5 mL) thrice, and lyophilised to yield the title compound as a dark orange oil which slowly crystallised (55 mg, 87 μmol, 90%). This material was used in a complexation reaction immediately, m/z (ESMS+) 658 (M+2Na), m.p. 120-1° C.

(iii) Preparation of Eu-Complex

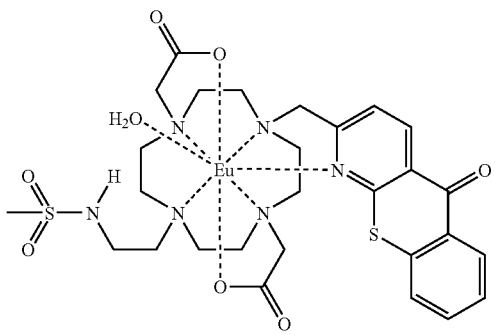

4-[(1-Azathioxanthone)-2-methyl]-10-[methylsulfonylamino)ethyl]-1,7-bis (carboxymethyl)-1,4,7,10-tetraazacyclododecane (28 mg, 44 μmol) was added to Eu(CF$_3$SO$_3$)$_3$ (1.1 eq., 26 mg) and the solids dissolved in a MeCN (2 mL) and the reaction left stirred at reflux temperature for 30 hrs. After the reaction was cooled to room temperature the solvents were removed under reduced pressure, the remaining residue was dissolved in 5 mL water:MeOH (5:1). The pH was then adjusted carefully to 10 by addition of conc. NaOH solution (in order to get rid of the Eu-excess as Eu(OH)$_3$) resulting in a white precipitates removed via a fine syringe filter. The pH was adjusted back to neutral and lyophilised to give a light brown solid, which has been loaded onto a DOWEX 1-X8(Cl) anionexchange resin. The column was eluted with water→10% NH$_4$OH and the fractions were analysed by ESMS+. The fractions were combined and lyophilised to yield the Eu-complex as a light brown powder. m/z (HRMS+) 819,09138 (C$_{28}$H$_{35}$O$_7$N$_6$S$_2$EuCl requires 819.09151)

EXAMPLE 4

Preparation of 4-[(1-Azathioxanthone)-2-methyl]-10-[methylsulfonylamino)ethyl]-1,7-bis(α-glutarate)-1,4,7,10-tetraazacyclododecane (i) Preparation of 1,7-Bis(α-dimethylglutarate)-1,4,7,10-tetraazacyclododecane

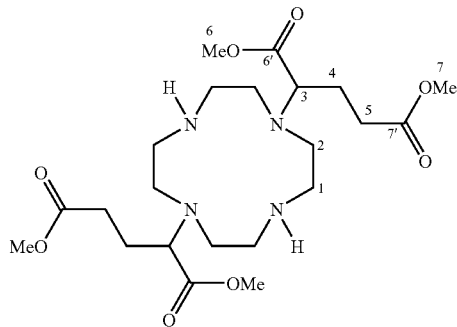

Tetraazacyclododecane (2.00 g, 11.61 mmol), dimethyl-2-bromoglutarate (6.10 g, 25.54 mmol) was dissolved in dry MeCN (20 mL) followed by addition of NaHCO$_3$ (2.14 g, 2.2 eq.). The mixture was stirred at 55° C. under argon. The reaction was monitored by TLC (DCM:MeOH:NH$_4$OH, 89:10:1) and ESMS+. After 7 days all dimethyl-2-bromoglutarate had been consumed, and the solvent was removed under reduced pressure. The remaining residue was dissolved in DCM (20 mL). The organic layer was washed with HCl (pH 3), dried over K$_2$CO$_3$ and the solvents removed under reduced pressure. The residue was purified by column chromatography over silica (DCM:THF:MeOH:NH$_4$OH, 25:65:5:5). The fractions containing the title product were combined and the solvents were removed under reduced pressure to yield a pale brown oil (1.23 g, 2.52 mmol, 21%) $\delta_H$ (CDCl$_3$) 7.68 (2H, br.s, NH), 3.63 (6H, s, H$^7$), 3.57 (6H, s, H$^6$), 3.26 (2H, m, H$^3$), 2.78 (16H, m, H$^{1,2}$), 2.36 (4H, m, H$^5$), 1.92 (4H, m, H$^4$) $\delta_c$ (CDCl$_3$) 173.4 (C$^7$), 172.9 (C$^{6'}$), 64.1 (C$^3$), 51.9 (CH$_3^6$), 51.8 (CH$_3^7$), 48.7, 46.5 (C$^{1,2}$), 30.0 (C$^5$), 22.6 (C$^4$), m/z (ESMS+) 489 (M+1), 490 (M+2), R$_f$ 0.32 (DCM:MeOH:NH$_4$OH, 89:10:1, silica plate)

(ii) Preparation of 4-[(1-Azathioxanthone)-2-methyl]-1,7-bis(α-dimethylglutarate)-1,4,7,10-tetraazacyclododecane

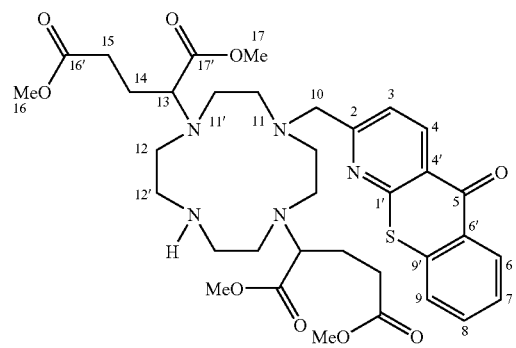

1,7-Bis(α-dimethylglutarate)-1,4,7,10-tetraazacyclododecane (320 mg, 0.66 mmol) was combined with 2-bromomethyl-1-azathiaxanthone (1 eq., 200 mg) and K$_2$CO$_3$ (1 eq., 91 mg) and the mixture stirred in dry MeCN (10 mL) at reflux under argon for 30 h. The reaction was monitored by TLC (DCM:MeOH, 97:3) and ESMS+ to confirm that the brominated starting material had been consumed. The solvent was removed under reduced pressure. The resulting solid was dissolved in a small volume of DCM (5 mL) and the KBr/K$_2$CO$_3$ was filtered out. The crude mixture was purified by column chromatography (DCM→2% MeOH) to yield the title compound as a pale brown oil (120 mg, 0.168 mmol, 26%) $\delta_H$(CDCl$_3$) 8.68 (1H, d, J 8.0 Hz, H$^4$), 8.43 (1H, m, H$^6$), 7.59 (2H, m, H$^{8,9}$), 7.42 (1H, m, H$^7$), 7.24 (1H, d, J 8.0 Hz, H$^3$), 3.83 (2H, s, H$^{10}$), 3.63 (6H, s, H$^{16}$), 3.57 (6H, s, H$^{17}$), 3.26 (2H, m, H$^{13}$), 2.97 (16H, m, H$^{11,11',12,12'}$), 2.36 (4H, m, H$^{15}$), 1.92 (4H, m, H$^{14}$) $\delta_c$ (CDCl$_3$) 180.5 (C$^5$) 173.4 (C$^{16}$), 172.9 (C$^{17}$), 161.4 (C$^2$), 158.6 (C$^{1'}$), 138.4 (C$^4$), 137.5 (C$^6$), 133.3 (C$^8$), 130.0 (C$^6$), 129.0 (C$^9$), 127.1 (C$^7$), 126.6 (C$^9$), 125.3 (C$^4$), 122.2 (C$^3$), 65.1 (C$^{13}$), 51.9 (C$^{17}$), 51.8 (C$^{16}$) 51.3, 50.4, 49.2, 46.5 (C$^{11,11',12,12'}$) 46.1 (C$^{10}$), 30.9 (C$^{15}$) 25.7 (C$^{14}$), m/z (ESMS+) 714 (M+1); R$_f$ 0.16 (DCM:MeOH, 97:3, alumina plate)

(iii) Preparation of 4-[(1-Azathioxanthone)-2-methyl]-10-[methylsulfonylamino)ethyl]-1,7-bis(α-dimethylglutarate)-1,4,7,10-tetraazacyclododecane

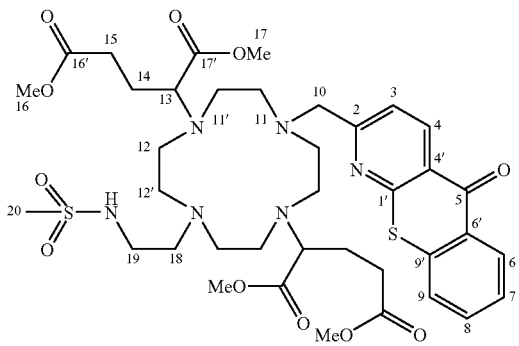

4-[(1-Azathioxanthone)-2-methyl]-1,7-bis(α-dimethylglutarate)-1,4,7,10-tetraazacyclododecane (110 mg, 0.15 mmol) was combined with N-methanesulfonyl-aziridine (1.1 eq., 19.4 mg) and $K_2CO_3$ (1 eq., 22 mg) stirred in dry MeCN (5 mL) at reflux under argon for 46 h. The reaction was monitored by TLC (DCM:MeOH, 97:3) and ESMS+ to confirm that the starting material had been consumed. The solvent was removed under reduced pressure. The resulting solid was dissolved in a small volume of DCM (3 mL) and the $K_2CO_3$ was filtered out. The crude mixture was purified by column chromatography (DCM→2% MeOH) to yield the title compound as a light brown oil which slowly crystallised (50 mg, 60 μmol, 41%). $\delta_H$ (CDCl$_3$) 8.70 (1H, d, J 8.0 Hz, H$^4$), 8.48 (1H, m, H$^6$), 7.63 (2H, m, H$^{8,9}$), 7.44 (2H, m, H$^{3,7}$), 3.83 (2H, s, H$^{10}$), 3.63 (6H, s, H$^{16}$), 3.60 (6H, s, H$^{17}$), 3.26 (2H, m, H$^{13}$), 3.02 (3H, s, H$^{20}$), 2.93 (16H, m, H$^{11,11',12,12'}$), 2.50 (6H, m, H$^{15,18}$), 1.90 (4H, m, H$^{14}$), 1.56 (2H, t, J 7.8 Hz, H$^{19}$) $\delta_c$ (CDCl$_3$) 180.5 (C$^5$) 173.3 (C$^{16'}$), 173.0 (C$^{17'}$), 162.1 (C$^2$), 158.8 (C$^{1'}$), 138.5 (C$^{4'}$), 137.5 (C$^{6'}$), 133.7 (C$^8$), 130.0 (C$^6$), 128.9 (C$^{9'}$), 127.2 (C$^7$), 126.6 (C$^9$), 125.5 (C$^4$), 122.7 (C$^3$), 65.9 (C$^{13}$), 51.7 (C$^{17}$), 51.4 (C$^{16}$), 54.2, 51.3, 49.2, 46.6 (C$^{11,11',12,12'}$), 46.1 (C$^{10}$), 38.1 (C$^{20}$), 33.4 (C$^{18}$), 30.9 (C$^{15}$) 25.7 (C$^{14}$) 22.9 (C$^{19}$), m/z (ESMS+) 835 (M+1); R$_f$ 0.39 (DCM:MeOH, 97:3, alumina), m.p. 137-9° C.

(iv) Preparation of 4-[(1-Azathioxanthone)-2-methyl]-10-[methylsulfonylamino)ethyl]-1,7-bis(α-glutarate)-1,4,7,10-tetraazacyclododecane

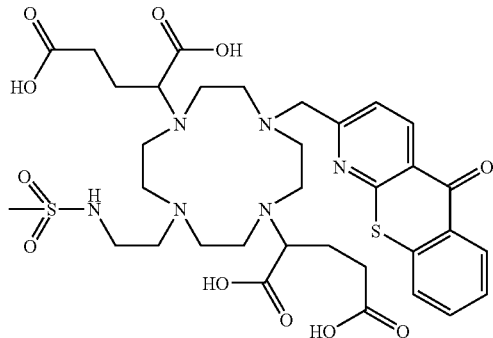

Freshly made 0.1 M KOD (2.5 mL) was added to 4-[(1-Azathioxanthone)-2-methyl]-10-[methylsulfonylamino) ethyl]-1,7-bis(α-dimethylglutarate)-1,4,7,10-tetraazacyclododecane (50 mg (60 μmol) the reaction had left under argon at room temperature and been monitored by NMR. After 3 h. no protecting methyl group signals were observed in the $^1$H-NMR spectrum The pH of the mixture was neutralised (pH≈6) with conc. HCL and loaded onto a DOWEX 1w50 strong cation exchange resin. The column was eluted with water→10% NH$_4$OH and the fractions were analysed by ESMS+. The fractions were combined and lyophilised to yiled the title compound as a dark orange oil (26 mg, 33 μmol, 55%), which has been used in a complexation reaction immediately, m/z (ESMS−) 779 (M−1)

(v) Preparation of Eu-Complex

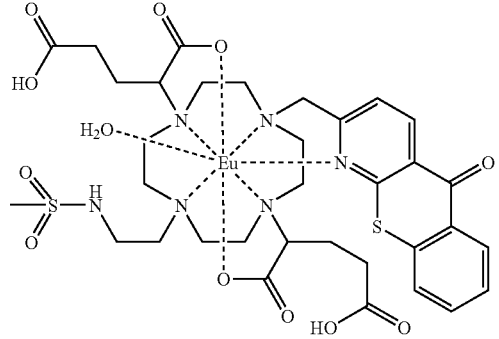

4-[(1-Azathioxanthone)-2-methyl]-10-[methylsulfonylamino)ethyl]-1,7-bis(α-glutarate)-1,4,7,10-tetraazacyclododecane (25 mg, 32 μmol) was added to Eu(CH$_3$CO$_2$)$_3$ (1.1 eq., 15 mg) and the solids dissolved in a H$_2$O (2 mL). The pH was carefully adjusted to 5 by addition of acetic acid and the reaction left to stir at 70° C. for 72 h. After the reaction was cooled to room temperature, the solvents were removed under reduced pressure, the remaining residue was dissolved in 5 mL H$_2$O. The pH was then adjusted carefully to 10 by addition of conc. NaOH solution (in order to get rid of the excess europium as Eu(OH)$_3$). This resulted in a white precipitate that was removed via a fine syringe filter. The pH was adjusted back to neutral and lyophilised to give a bright yellow solid. m/z (HRMS+) 927.1564 (C$_{234}$H$_{42}$O$_{11}$N$_6$S$_2$Eu requires 927.1565)

The invention claimed is:

1. A compound comprising a xanthone or thiaxanthone sensitizing moiety having an integral pyridyl group that constitutes part of the moiety, the integral pyridyl group having a nitrogen atom capable of coordinating to a lanthanide ion, wherein the compound has any one of the following formulae 1 and 2:

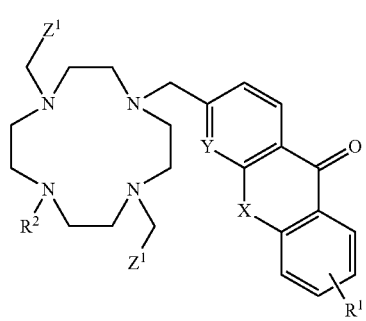

1

-continued

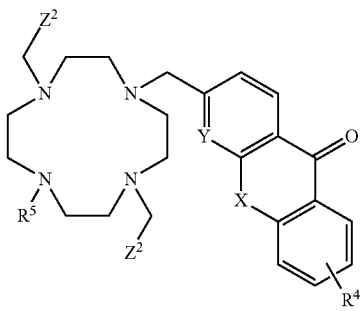

wherein:
R¹ is H, alkyl, aralkyl, $CO_2R^3$, or $CONHR^3$;
R² is H, alkyl or aralkyl;
R³ is alkyl, aralkyl or aryl, optionally substituted;
R⁴ is H, alkyl, aralkyl, or $CO_2R^6$;
R⁵ is $CH_2CH_2NHSO_2R^6$;
R⁶ is alkyl, p-R⁴-Ph, p-OMe-Ph, or p-$CF_3$-Ph;
X is O or S;
Y is the nitrogen atom capable of coordinating and binding to the lanthanide ion;
Z¹ is $CO_2^-$, $PR^1O_2^-$, $PO_3^{2-}$, or $CONHR^3$; and
Z² is $CO_2^-$, $PR^4O_2^-$, $PO_3^{2-}$, or $CONHR^4$.

2. The compound as claimed in claim 1 having formula 1.

3. The compound as claimed in claim 1 which is 1-(2'-[1-azathioxanthone]methyl)-4,10-bis[(S,S)-ethyl-2"-carbamoylmethyl-3-phenylpropanoate]-1,4,7,10-tetra-azacyclododecane.

4. The compound as claimed in claim 1 which is 4-[(1-azathioxanthone)-2-methyl]-1,7-bis(carboxylmethyl)-1,4,7,10-tetra-azacyclododecane, 4-[(1-azathioxanthone)-2-methyl]-10-[methylsulfonylamino)ethyl]-1,7-bis(carboxylmethyl)-1,4,7,10-tetraazacyclododecane or 4-[(1-azathioxanthone)-2-methyl]-10-[methylsulfonylamino)ethyl]-1,7-bis(α-glutarate)-1,4,7,10-tetraazacyclododecane.

5. A complex of a compound as defined in claim 1 with a lanthanide (III) ion.

6. The complex as claimed in claim 5 wherein the lanthanide ion is terbium.

7. The complex as claimed in claim 5 wherein the lanthanide ion is europium.

8. The complex comprising a compound as defined in claim 1 with a lanthanide (III) ion having any one of the following structures 4 and 5:

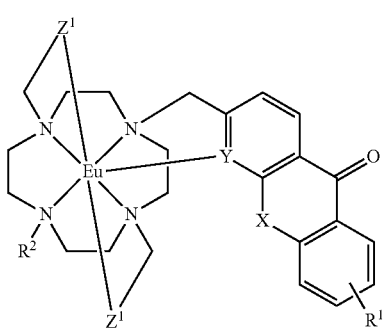

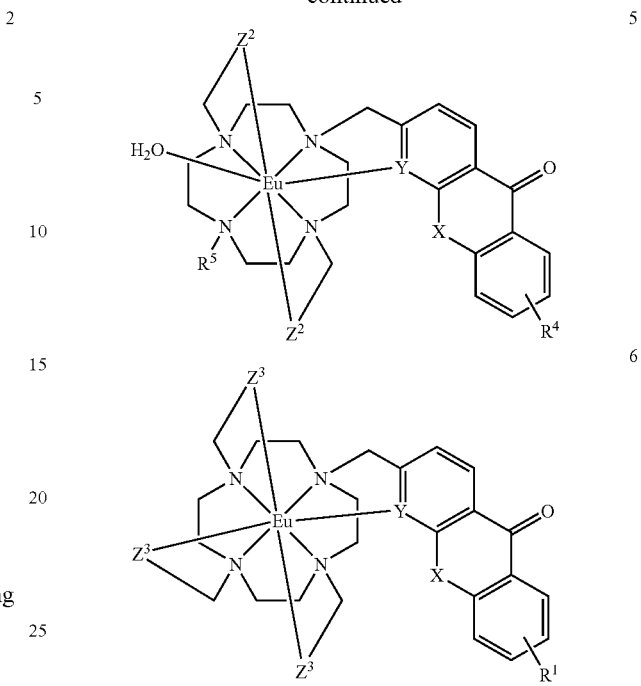

wherein Ln is the lanthanide (III) ion.

9. A method of modulating a complex as defined in claim 5 comprising reacting the complex with a ligand.

10. The method of claim 9 wherein said ligand is an anion.

11. The method of claim 10 wherein the anion is a phosphonoanion, citrate, lactate or hydrogencarbonate.

12. The method of claim 11 wherein the anion is citrate.

13. The method of claim 12 wherein the method is used to signal variation in the concentration of the citrate anion.

14. A method of modulating a complex as defined in claim 5 comprising subjecting the solution to complex to a pH change.

15. The method of claim 14 wherein the pH is varied over the range 3 to 9.

16. The method of claim 14 wherein the pH is varied over the range 4.5 to 8.

17. The method of claim 14 wherein the method is used to monitor local pH changes using monitoring local pH changes in real time in a ratiometric analytical method.

18. The method of claim 17 wherein the analytical method is conducted as part of an in vitro, in cellulo or in vivo assay or application.

19. The method of claim 18 wherein said assay or application the analytical method is conducted as part of an in vitro assay or application.

20. The method of claim 18 wherein said assay or application involves time-resolved luminescence using microscopy or spectroscopy.

21. The compound as claimed in claim 1 having formula 2.

* * * * *

UNITED STATES PATENT AND TRADEMARK OFFICE
CERTIFICATE OF CORRECTION

PATENT NO.         : 8,193,174 B2
APPLICATION NO.    : 11/913991
DATED              : June 5, 2012
INVENTOR(S)        : David Parker, Robert Pal and Junhua Yu Page 1 of 1

It is certified that error appears in the above-identified patent and that said Letters Patent is hereby corrected as shown below:

On the title page, item 12, change "David et al." to --Parker et al.--.

On the title page, item 75, Inventors, change "Parker David" to --David Parker--.

In the claims

In column 17, line 34, after "10-tetra-azacyclododecane" delete the "," and insert --or--.

In column 17, line 36, after "(carboxylmethyl)-1,4,7,10-tetraazacyclododecane" insert --.-- and delete "or 4-[(1-".

In column 17, line 37, delete "azathioxanthone)-2-methyl]-10-[methylsulfonylamino)".

In column 17, line 38, delete "ethyl]-1,7-bis(alpha-glutarate)-1,4,7,10-tetraazacyclododecane.".

Signed and Sealed this
Fifth Day of July, 2016

Michelle K. Lee
*Director of the United States Patent and Trademark Office*